United States Patent
Saerens et al.

(10) Patent No.: US 10,647,951 B2
(45) Date of Patent: May 12, 2020

(54) PRODUCTION OF A LOW-ALCOHOL FRUIT BEVERAGE

(71) Applicant: Chr. Hansen A/S, Hoersholm (DK)

(72) Inventors: Sofie Saerens, Skovlunde (DK); Nathalia Edwards, Frederiksberg (DK); Kim Ib Soerensen, Farum (DK); Mansour Badaki, Vanloese (DK); Jan Hendrik Swiegers, Fredensborg (DK)

(73) Assignee: CHR. HANSEN A/S, Hoersholm (DK)

( * ) Notice: Subject to any disclaimer, the term of this patent is extended or adjusted under 35 U.S.C. 154(b) by 158 days.

(21) Appl. No.: 15/112,966

(22) PCT Filed: Jan. 21, 2015

(86) PCT No.: PCT/EP2015/051163
§ 371 (c)(1),
(2) Date: Jul. 20, 2016

(87) PCT Pub. No.: WO2015/110484
PCT Pub. Date: Jul. 30, 2015

(65) Prior Publication Data
US 2016/0376537 A1 Dec. 29, 2016

(30) Foreign Application Priority Data

Jan. 21, 2014 (EP) .................................. 14151980
May 21, 2014 (EP) .................................. 14169278

(51) Int. Cl.
*C12G 1/022* (2006.01)
*C12R 1/25* (2006.01)
*C12N 1/20* (2006.01)

(52) U.S. Cl.
CPC ............. *C12G 1/0203* (2013.01); *C12N 1/20* (2013.01); *C12R 1/25* (2013.01); *C12G 2200/05* (2013.01)

(58) Field of Classification Search
USPC .............................. 426/590, 592, 13, 11, 15
See application file for complete search history.

(56) References Cited

FOREIGN PATENT DOCUMENTS

| CH | 668 887 A5 | 2/1989 |
|---|---|---|
| CN | 1710047 A | 12/2005 |
| CN | 101904525 A | 12/2010 |
| CN | 102161958 A | 8/2011 |
| CN | 102358888 A | 2/2012 |
| DE | 39 39 064 A1 | 5/1991 |
| DE | 42 39 605 A1 | 5/1994 |
| DE | 197 30 538 A1 | 1/1999 |
| EP | 0 113 055 | 7/1984 |
| JP | 2005-192562 | 7/2005 |
| KR | 10-2010-0101723 | 9/2010 |
| WO | WO 89/06685 | 7/1989 |
| WO | WO 2012/172000 | 12/2012 |

OTHER PUBLICATIONS

Ciani and Ferraro; "Enhanced Glycerol Content in Wines Made with Immobilized Candida stellata Cells"; *Applied and Environmental Microbiology*, 62(1): 128-132, (Jan. 1996).

Comitini et al.; "Selected non-*Saccharomyces* wine yeasts in controlled multistarter fermentations with *Saccharomyces cerevisiae*"; *Food Microbiology*, 28(5): 873-882, (Aug. 2011)(available online Dec. 2010).

Contreras et al.; "Evaluation of non-*Saccharomyces* yeast for the reduction of alcohol content in wine"; *Applied Environment Microbiol*, 80(5):1670-78 (Dec. 2013).

Di Maio et al; "A method to Discriminate between the *Candida stellate* and *Saccharomyces cerevisiae* in mixed fermentation on WLD and Lysine Agar Media"; *South African Journal of Enology and Viticulture*, 32(1): 35-41 (Jan. 2011).

Di Maio et al.; "Presence of Candida zemplinina in Sicilian musts and selection of a strain for wine mixed fermentations"; *South African Journal of Enology and Viticulture*, 33(1): 80-87 (Jan. 2012).

Erten and Campbell; "The Production of Low-Alcohol Wines by Aerobic Yeasts"; *Journal of the Institute of Brewing*, 107(4): pp. 207-215 (2001).

Ferraro et al.; "Pilot scale vinification process using immobilized *Candida stellata* cells and *Saccharomyces cerevisiae*"; *Process Biochemistry*, 35(10): 1125-1129 (Jul. 2000).

Garcia et al; "Effects of using mixed wine yeast cultures in the production of Chardonnay wines"; *Revista Argentina de Microbiologia*, 42(3): 226-229 (Jul. 2010).

Servetas et al.; "*Saccharomyces cervisiae* and *Oenococcus oeni* immobilized in different layers of a cellulose/starch gel composite for simultaneous alcoholic and malolactic wine fermentations"; *Process Biochemistry*, 48(9): 1279-1284 (Sep. 2013)(available online Jun. 2013).

Kolb et al.; "Biological processes for the partial reduction of sugar in fruit juices"; Proceedings of the International Federation of Fruit Juice Producers Symposium, Budapest, 7-20 (1993).

Kutyna et al.; "Microbiological approaches to lowering ethanol concentrations in wine"; *Trends in Food Science and Technology*, 21(6): 293-302 (Jun. 2010)(available online Mar. 2010).

Laplace et al.; "Incidence of indigenous microbial flora from utensils and surrounding air in traditional French cider making"; *Journal of the Institute of Brewing*, 104(2): 71-74 (Mar. 1998).

Lerm et al.; "Selection and Characterisation of *Oenococcus oeni* and *Lactobacillus plantarum* South African Wine Isolates for Use as Malolactic Fermentation Starter Cultures"; *South African Journal of Enology and Viticulture*, 32(2): 280-295 (Dec. 2011).

Martinez-Anaya et al.; "Biochemical characteristics and breadmaking performance of freeze-dried wheat sour dough starters"; *Zeitschrift für Lebensmittel untersuchung und Forschung*, 196(4): 360-365 (Apr. 1993).

(Continued)

*Primary Examiner* — Vera Stulii
(74) *Attorney, Agent, or Firm* — Foley & Lardner LLP

(57) ABSTRACT

The present invention relates to the production of fermented fruit beverages, such as wine and cider, with a reduced level of alcohol. Specifically, the present invention is directed to a method for producing a beverage with a reduced content of alcohol comprising using reverse inoculation or co-inoculation of homofermentative or facultative heterofermentative lactic acid bacterium strain and a yeast strain.

9 Claims, 8 Drawing Sheets

(56) References Cited

OTHER PUBLICATIONS

Maygar and Tóth; "Comparative evaluation of some oenological properties in wine strains of *Candida stellata, Candida zemplinina, Saccharomyces uvarum* and *Saccharomyces cerevisiae*"; *Food Microbiology*, 28(1): 94-100 (Feb. 2011)(available online Sep. 2010).
Passos et al.; "Effect of malic acid on the growth kinetics of *Lactobacillus plantarum*"; *Applied Microbiology and Biotechnology*, 63(2): 207-211 (Dec. 2003)(available online Jun. 2003).
Pickering; "Low- and reduced-alcohol wines: A review"; *Journal of Wine Research*, 11(2): 129-144 (2000).
Sadoudi et al.; "Yeast-yeast interactions revealed by aromatic profile analysis of Sauvignon Blanc wine fermented by single or co-culture of non-*Saccharomyces* and *Saccharomyces* yeasts"; *Food Microbiology*, 32(2): 243-253 (Dec. 2012)(available online Jul. 2012).
Schmidtke et al.; "Production technologies for reduced alcoholic wines"; *Journal of Food Science*, 71(1): 25-41 (Jan. 2012)(available online Nov. 2011).
Smith; "Biological processes for the reduction of alcohol in wines"; Master of Applied Science, dissertation, Lincoln University, New Zealand, (1995).
International Search Report issued in application PCT/EP2015/051163 dated Oct. 9, 2015.
Zhao et al., "A Study on Fermentation Fruit-Tea Juice Using Mixed Species of Microorganisms," *Journal of Sichuan Institute of Light Industry and Chemical Technology*, vol. 9, No. 2, pp. 21-25 (Jun. 1996).
Chinese Office Action issued in co-peding Chinese Patent Application No. 2015800052687, dated Jan. 23, 2019.

PRODUCTION OF A LOW-ALCOHOL FRUIT BEVERAGE

FIELD OF THE INVENTION

The present invention relates to the production of fermented fruit beverages, such as wine and cider, with a reduced level of alcohol. Specifically, the present invention is directed to a method for producing a beverage with a reduced content of alcohol comprising using reverse inoculation or co-inoculation of a homofermentative or facultative heterofermentative lactic acid bacterium strain and a yeast strain.

BACKGROUND OF THE INVENTION

Today, as a consequence of greater social and health awareness with consumers, there is a high demand in the wine world for solutions to decrease the alcohol content in the final wine. As an alternative to full-strength wines, wines with a reduced alcohol content offer a number of potential social and health benefits for consumers. Social benefits may include improved productivity and function after activities involving alcohol (e.g. business lunches), lower risk of accidents while driving and more acceptable social behavior in general. Health advantages may include reduced calorie intake, decreased risk of alcohol-related illness and disease and specific benefits for pregnant women. For the producers of these wines, there exists an incentive of identified markets and market segments, as well as lower sales and duty taxes applicable in many countries (Pickering, 2000).

Methods for producing reduced-alcohol wines have been available since the early 1900s. Although commercial production nowadays relies almost exclusively on systems based on the use of membranes and modified distillation, a number of alternative approaches have been put forward in literature. These approaches are summarized in Table 1 (Pickering, 2000).

TABLE 1

Current techniques for producing reduced-alcohol wines (adapted from Pickering, 2000 and Schmidtke et al. 2012)

| Principle | Method |
|---|---|
| Reduction of fermentable sugar concentration in grape or juice | Use of unripe fruit<br>Juice dilution<br>Freeze concentration and fractionation<br>Enzymes (e-g- glucose oxidase) |
| Removal of alcohol from wine | Thermal: distillation, evaporation or freeze concentration<br>Membrane: dialysis or reverse osmosis<br>Adsorption: resins or silica gel<br>Extraction: organic solvents or supercritical $CO_2$<br>Modified yeast strains |
| Other | Dilution of wine<br>Arresting fermentation early<br>Low-alcohol-producing yeast<br>Combinations of above methods |

When using unripe fruit and/or diluted juice/must, the flavor of the final wine is compromised, due to the lower concentration of flavor precursors. Mechanical removal of ethanol tends to be a harsh process that affects the overall chemical composition of the wine, and thereby also the sensory profile and experience of the wine.

A lot of work has been done so far in reducing sugar with a biological approach. Five different methods have been explored: 1) aeration of the must during fermentation using *Saccharomyces* sp. with a conversion of sugar to $CO_2$, water and biomass, 2) aeration of the must during fermentation using non-*Saccharomyces* sp. with a conversion of sugar to $CO_2$, water and biomass, 3) the use of non-*Saccharomyces* and *Saccharomyces* sp. in a sequential fermentation, 4) early arrest of fermentation for the production of sweet wines and 5) genetically modified *Saccharomyces cerevisiae* wine strains to redirect ethanol production.

Lowering alcohol percentage by aeration of the must during fermentation using *Saccharomyces* sp. has been explored since 1989. A process has been described for the preparation of low-sugar or sugar-free fruit juices based on continuous or semi-continuous culture with yeast, with the conditions resulting in metabolism of sugar to $CO_2$ and water rather than to ethanol and so recovering an alcohol-free, sugar-free or low sugar juice by separation of the biomass (Kaeppeli, 1989). A similar system is described by Grossmann et al. (1991) for producing low-alcohol drinks, where oxygen is added to the fermenting liquid in a controlled manner in order to convert the sugars to water and $CO_2$. The supply of oxygen is interrupted when the required level of residual alcohol is reached, then the yeast is separated from the liquid, and finally the liquid is microfiltered in order to produce a clear liquid product.

By screening a broad collection of yeast species, Kolb et al (1993) found that *Pichia stipitis* was particularly well suited for juice sugar removal. Their claims include the elimination of more than 50% of juice sugar within 20 h, and a minimum of adverse effects on the sensory and functional qualities of the juice. Similar results have been obtained by investigating the effect of varying aeration and temperature levels on the reduction of sugar and production of alcohol in Muller-Thurgau grape juice by selected yeast strains (Smith et al. 1995). Seven yeast strains showed promising results of which three strains produced significant alcohol reductions: *Pichia stipitis, Candida tropicalis* and *Saccharomyces cerevisiae*. By combining short-term controlled aeration, to reduce the sugar content, with anaerobic fermentation using an active dried wine yeast, wines with acceptable taste and 25 to 30% less alcohol were produced. However, these wines exhibited the deep golden color indicative of oxidation, which generally is undesired in wine.

More investigations into mixed starter cultures of non-*Saccharomyces* species with a *Saccharomyces cerevisiae* wine strain revealed that the alcohol percent (v/v) could be reduced with 0.2-0.7% (Ciani and Ferraro, 1996; Ferraro et al. 2000; Erten and Campbell, 2001; Ciani et al. 2006; Garcia et al. 2010; Maygar and Toth, 2011; Comitini et al. 2011; Di Maio et al. 2012; Sadoudi et al. 2012). In a recent publication of the Australian Wine Research Institute (AWRI), evaluation of 50 different non-*Saccharomyces* isolates, belonging to 24 different genera, has been performed for their capacity to produce wine with lower ethanol concentration when used in sequential inoculation regimes with a *Saccharomyces cerevisiae* wine strain (Contreras et al. 2013). A sequential inoculation of *Metschnikowia puicherrima* AWRI1149 followed by a *Saccharomyces cerevisiae* wine strain was the best combination able to produce wine with a lower ethanol concentration than the single-inoculum, wine yeast, control. Sequential fermentations utilizing AWRI1149 produced wines with 0.9% (v/v) and 1.6% (v/v) (corresponding to 7.1 g/L and 12.6 g/L) less ethanol concentration in Chardonnay and Shiraz, respectively.

Another approach of lowering ethanol in wine production is the use of genetically modified yeast strains (Kutyna et al., 2010). However, with the current consumer reluctance against the use of GMO yeast strains in wine, this option is not considered to be commercially viable at this moment.

Currently, the mentioned methods have a limited commercial application. The main problem is the reduced sensory quality compared with full-strength wine. In particular, problems with flavor imbalance and a lack of 'body' have been reported. The main flavor compound resulting in an imbalanced flavor profile is ethyl acetate, which is often found in very high concentrations in the reduced alcohol wines produced with the current methods. These altered sensory properties can occur as a result of the processing required to produce the reduced alcoholic wine or as a direct consequence of the reduced ethanol content. The main characteristics of the biological approaches to reduced alcohol wines is the potential off-flavor development (too high acetic acid or ethyl acetate concentrations) with the use of non-*Saccharomyces* yeast strains or oxidation of the final wine when aeration techniques are used, resulting in undesirable organoleptic characters.

SUMMARY OF THE INVENTION

The problem to be solved by the present invention is the provision of an alternative method for reducing the alcohol content in fermented fruit beverages without a loss in sensory quality of the wine.

The solution is based on the surprising finding by the inventors that a homofermentative or facultative heterofermentative lactic acid bacterium strain (known as Group I and II), when inoculated prior to or simultaneously with yeast fermentation, can be used to lower the alcohol content in wine with at least 0.5% (v/v) compared to the wine made by fermentation with the yeast only.

The inventors observed that the lactic acid bacterium uses the sugar in the must to form lactic acid (and other metabolites) without producing ethanol. In this way, ethanol can be reduced in the final wine, without any negative influence on flavor profile.

Moreover, it seems that the fruity notes as well as the round mouth feel are enhanced in these wines.

On top of that, also the malic acid may be converted to lactic acid by the homofermentative or facultative heterofermentative *Lactobacillus* spp. strains tested, meaning that the malolactic fermentation (MLF) is performed during the alcoholic fermentation.

This means that by using this new technique, winemakers can reduce alcohol and complete MLF at the same time, without compromising flavor.

In comparison to the current state-of-the-art biological approaches to lower alcohol by using either oxygen in combination with a *Saccharomyces* or non-*Saccharomyces* yeast or by using non-*Saccharomyces* strains with lower sugar to ethanol conversion, the present technique of using homofermentative or facultative heterofermentative lactic acid bacterium strains in reverse inoculation (the lactic acid bacterium strain is inoculated prior to fermentation with the yeast) or co-inoculation (the lactic acid bacterium strain is inoculated at the same time as fermentation with the yeast) with a wine yeast does not result in wine oxidation, flavor imbalance or lack of mouth feel, but may even improve the flavor profile of the wine.

DETAILED DISCLOSURE OF THE INVENTION

One aspect of the present invention relates to a method for producing a beverage with a reduced content of alcohol comprising the steps of:

a) inoculating and fermenting a fruit must with at least one homofermentative or facultative heterofermentative lactic acid bacterium strain; and
b) simultaneously or within a period of time after adding the at least one homofermentative or facultative heterofermentative lactic acid bacterium strain, fermenting the fruit must with at least one yeast strain to obtain the beverage with a reduced content of alcohol compared to the beverage fermented with the yeast strain alone.

In a preferred embodiment, the fermentation of the fruit must with a yeast strain in step b) is carried out at least 12 hours, such as 24 hours, such as 36 hours, such as 48 hours, such as 60 hours, after adding the at least one homofermentative or facultative heterofermentative lactic acid bacterium strain.

In a further preferred embodiment the fermentation of the fruit must with a yeast strain in step b) is carried out within 72 hours, such as within 60 hours, such as within 48 hours, such as within 24 hours, such as within 12 hours.

Another aspect of the present invention relates to a beverage obtainable by the method according to the previous aspect.

In one other aspect the present invention relates to a method for producing a beverage with a reduced content of alcohol comprising the steps of:

a) inoculating and fermenting a fruit must with a homofermentative or facultative heterofermentative lactic acid bacterium strain; and
b) simultaneously or after a period of time adequate to convert at least a portion of the sugar to lactic acid or other metabolites fermenting the fruit must with a yeast strain to obtain the beverage with a reduced content of alcohol compared to the beverage fermented with the yeast strain alone.

The term "reduced content of alcohol" in a beverage as used herein relates to a lower concentration of alcohol in the beverage as compared to a beverage prepared under identical conditions but without the addition of the homofermentative or facultative heterofermentative lactic acid bacterium strain.

As used herein, the term "must" designates the unfermented or fermenting juice expressed from grapes or other fruits.

The term "wine", as used herein, refers to a must, in which the alcohol quantity produced by alcoholic fermentation is at least 4% (v/v), including but not limited to fermented grape must (red wine, white wine, sparkling wine etc.) and cider (fermented fruit must based on juice from apple, pear, peach etc.). The wine may have reached its maximum alcoholic degree if the alcoholic fermentation is ended. The alcohol contents are expressed by the volume of alcohol in relation to the total volume.

Homofermentative lactic acid bacteria ferment glucose and/or fructose with lactic acid as the primary by-product.

Heterofermentative lactic acid bacteria ferment glucose and/or fructose with lactic acid, ethanol/acetic acid and carbon dioxide as by-products. Facultative heterofermentative lactic acid bacteria produce carbon dioxide and other by-products only under certain conditions or from specific substrates.

The group of homofermentative and facultative heterofermentative lactic acid bacterium strains include strains of *Lactobacillus acidophilus, Lactobacillus casei, Lactobacillus paracasei, Lactobacillus crispatus, Lactobacillus curvatus, Lactobacillus delbrueckii, Lactobacillus gallinarum, Lactobacillus gasseri, Lactobacillus helveticus, Lactobacil-*

*lus jensenii, Lactobacillus johnsonii, Lactobacillus kefiranofaciens, Lactobacillus pentosus, Lactobacillus plantarum, Lactobacillus rhamnosus, Lactobacillus sake, Lactobacillus salivarius, Lactococcus lactis, Leuconostoc mesenteroides, Pediococcus acidilactici, Pediococcus damnosus, Pediococcus dextrinicus, Pediococcus pentocaceus, Pediococcus parvulus* and *Streptococcus thermophilus*.

In a preferred embodiment the fruit must is inoculated and fermented with at least two or more homofermentative and facultative heterofermentative lactic acid bacterium strain in step a), such as 2, 3, 4, 5 or more homofermentative and facultative heterofermentative lactic acid bacterium strains.

In a preferred embodiment the homofermentative or facultative heterofermentative lactic acid bacteria is a homofermentative or facultative heterofermentative *Lactobacillus* spp. strain.

In a preferred embodiment the homofermentative or facultative heterofermentative *Lactobacillus* spp. strain is selected from the group consisting of a *Lactobacillus plantarum* strain and a *Lactobacillus paracasei* strain.

In an even more preferred embodiment the homofermentative or facultative heterofermentative *Lactobacillus* spp. strain is a *Lactobacillus plantarum* strain.

Preferably, the *Lactobacillus plantarum* strain is selected from the group consisting of the *Lactobacillus plantarum* strain CHCC12399 that was deposited with the German Collection of Microorganisms and Cell Cultures (DSMZ) under accession No. DSM 27565, and a mutant strain thereof, wherein the mutant strain is obtained by using the deposited strain as starting material, and wherein the mutant strain reduces the content of alcohol in a beverage when used to inoculate and ferment a fruit must prior to or simultaneously with fermentation of the fruit must with a yeast strain as compared to the beverage fermented with the yeast strain alone.

In the present context, the term "mutant strain" should be understood as a strain derived from a strain of the invention by means of e.g. genetic engineering, radiation and/or chemical treatment, and/or selection, adaptation, screening, etc. It is preferred that the mutant is a functionally equivalent mutant, e.g. a mutant that has substantially the same, or improved, properties (e.g. the capability of reducing the content of alcohol in a beverage when used to inoculate and ferment a fruit must prior to or simultaneously with fermentation of the fruit must with a yeast strain according to the method of the present invention as compared to the beverage fermented with the yeast strain alone) as the mother strain. Such a mutant is a part of the present invention. Especially, the term "mutant strain" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, no more than 10, or no more than 5, treatments are carried out. In a presently preferred mutant, less than 1%, or less than 0.1%, less than 0.01%, less than 0.001% or even less than 0.0001% of the nucleotides in the bacterial genome have been changed (such as by replacement, insertion, deletion or a combination thereof) compared to the mother strain.

It was shown in the Examples below that when the bacteria are inoculated at relatively low concentrations the amount of bacteria inoculated in step a) determines the period of time adequate to convert at least a portion of the sugar to lactic acid. Furthermore, it was shown, that when the bacteria were inoculated at relatively high concentrations, it was possible to co-inoculate the bacteria and the yeast and still achieve a reduction in the content of alcohol in the beverage.

Thus, in a preferred embodiment the homofermentative or facultative heterofermentative lactic acid bacterium strain is inoculated in an amount of at least $1 \times 10^4$ CFU/ml, such as at least $5 \times 10^4$ CFU/ml, such as at least $1 \times 10^5$ CFU/ml, such as at least $5 \times 10^5$ CFU/ml, such as at least $1 \times 10^6$ CFU/ml, such as at least $5 \times 10^6$ CFU/ml, such as at least $1 \times 10^7$ CFU/ml, and the fruit must is fermented for a period of time adequate to convert at least a portion of the sugar to lactic acid or other metabolites before the fermentation with the yeast strain.

Preferably, the period of time adequate to convert at least a portion of the sugar to lactic acid or other metabolites is at least 12 hours, such as at least 24 hours, such as at least 36 hours, such as at least 48 hours, such as at least 52 hours, such as at least 60 hours, such as at least 72 hours.

In a more preferred embodiment, the portion of the sugar which is converted to lactic acid or other metabolites is at least 5 g/L, such as at least 10 g/L, such as at least 15 g/L, such as at least 20 g/L.

In another preferred embodiment the homofermentative or facultative heterofermentative lactic acid bacterium strain is inoculated in an amount of at least $1 \times 10^4$ CFU/ml, such as at least $5 \times 10^4$ CFU/ml, such as at least $1 \times 10^5$ CFU/ml, such as at least $5 \times 10^5$ CFU/ml, such as at least $1 \times 10^6$ CFU/ml, such as at least $5 \times 10^6$ CFU/ml, such as at least $1 \times 10^7$ CFU/ml, such as at least $5 \times 10^7$ CFU/ml, such as at least $1 \times 10^8$ CFU/ml, and the fruit must is fermented simultaneously with the lactic acid bacterium strain and the yeast strain.

In an especially preferred embodiment the homofermentative or facultative heterofermentative lactic acid bacterium strain is a *Lactobacillus plantarum* strain.

In one preferred embodiment the fruit must is fermented with a yeast strain which is inoculated in an amount of at least $1 \times 10^5$ CFU/ml, such as at least $5 \times 10^5$ CFU/ml, at the onset of yeast fermentation in step b).

In another preferred embodiment the fruit must is fermented spontaneously in step b) with an indigenous yeast.

The yeast which is used may be any type of yeast which is used in the beverage or food industry. Examples include e.g. *Pichia kluyveri, Saccharomyces cerevisiae, Saccharomyces pastorianus, Saccharomyces bayanus, Torulaspora delbrueckii*, or *Kluyveromyces thermotolerans* etc.

Typical yeasts used in wine production are from the yeast family Saccharomycetaceae (ascomycetous yeasts). Yeasts from the genus *Saccharomyces* (e.g. the species *Saccharomyces cerevisiae*) are commonly used. Other used yeasts are from the same Saccharomycetaceae family but from other genera such as *Kluyveromyces* (e.g. the species *Kluyveromyces thermotolerans*) and the genus *Torulaspora* (e.g. the species *Torulaspora delbrueckii*).

For the inoculation of a fruit must, a pure yeast culture may be used (i.e. a culture containing only one type of yeast), but a mixed culture of two or more types of yeast may also be used as inoculant.

In a preferred embodiment the fruit must is inoculated and fermented with at least two or more yeast strains in step b), such as 2, 3, 4, 5 or more yeast strains.

The method according to the invention allows for significant reduction in the alcohol concentration of a beverage:

Example 1 herein shows more than 1% (v/v) reduction of alcohol concentration from 9.5% (v/v), 9.0% (v/v) and 10.2% (v/v).

Example 2 herein shows more than 1% (v/v) reduction in alcohol concentration from 10.2% (v/v).

Example 3 herein shows 0.95%, 0.55% and 1.4% reduction of alcohol concentration from 10.05% (v/v).

Example 4 herein shows 1.1% (v/v) and 0.9% (v/v) reduction of alcohol concentration from 14.14% (v/v) and 13.25% (v/v), respectively.

Example 5 herein shows 0.6% (v/v) reduction of alcohol concentration from 8.45% (v/v).

Accordingly, in a preferred embodiment, the alcohol concentration of the beverage is at least 0.5% (v/v), such as at least 0.75% (v/v), such as at least 1% (v/v), such as at least 1.25% (v/v), such as at least 1.5% (v/v), such as at least 1.75% (v/v), such as at least 2% (v/v), such as at least 2.5% (v/v), such as at least 3% (v/v), lower than the alcohol concentration of a beverage prepared under identical conditions but without the addition of the homofermentative or facultative heterofermentative lactic acid bacterium strain.

Another aspect of the present invention relates to a beverage obtainable by the method according to the previous aspect.

Furthermore, an aspect of the present invention is directed to a Lactobacillus plantarum strain selected from the group consisting of the Lactobacillus plantarum strain CHCC12399 that was deposited with the German Collection of Microorganisms and Cell Cultures (DSMZ) under accession No. DSM 27565, and a mutant strain thereof, wherein the mutant strain is obtained by using the deposited strain as starting material, and wherein the mutant strain reduces the content of alcohol in a beverage when used to inoculate and ferment a fruit must prior to or simultaneously with fermentation of the fruit must with a yeast strain as compared to the beverage fermented with the yeast strain alone.

An even further aspect relates to use of a homofermentative or facultative heterofermentative lactic acid bacterium strain for reducing alcohol content in a beverage.

In a preferred embodiment the homofermentative or facultative heterofermentative lactic acid bacterium strain is a homofermentative or facultative heterofermentative Lactobacillus spp. strain.

Preferably, the homofermentative or facultative heterofermentative Lactobacillus spp. strain is selected from the group consisting of a Lactobacillus plantarum strain and a Lactobacillus paracasei strain.

In a preferred embodiment, the Lactobacillus plantarum strain is selected from the group consisting of the Lactobacillus plantarum strain CHCC12399 that was deposited with the German Collection of Microorganisms and Cell Cultures (DSMZ) under accession No. DSM 27565, and a mutant strain thereof, wherein the mutant strain is obtained by using the deposited strain as starting material, and wherein the mutant strain reduces the content of alcohol in a beverage when used to inoculate and ferment a fruit must prior to or simultaneously with fermentation of the fruit must with a yeast strain as compared to the beverage fermented with the yeast strain alone.

Yet another aspect of the present invention is directed to a kit comprising a homofermentative or facultative heterofermentative lactic acid bacterium strain and a yeast strain.

In a preferred embodiment the homofermentative or facultative heterofermentative lactic acid bacterium is a homofermentative or facultative heterofermentative Lactobacillus spp.

In a preferred embodiment the homofermentative or facultative heterofermentative Lactobacillus spp. strain is selected from the group consisting of a Lactobacillus plantarum strain and a Lactobacillus paracasei strain.

Preferably, the Lactobacillus plantarum strain is selected from the group consisting of the Lactobacillus plantarum strain CHCC12399 that was deposited with the German Collection of Microorganisms and Cell Cultures (DSMZ) under accession No. DSM 27565, and a mutant strain thereof, wherein the mutant strain is obtained by using the deposited strain as starting material, and wherein the mutant strain reduces the content of alcohol in a beverage when used to inoculate and ferment a fruit must prior to or simultaneously with fermentation of the fruit must with a yeast strain as compared to the beverage fermented with the yeast strain alone.

In a more preferred embodiment the kit further comprises instructions on how to use the kit to produce a beverage with a reduced content of alcohol.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes Lactococcus spp., Streptococcus spp., Lactobacillus spp., Leuconostoc spp., Pediococcus spp., Brevibacterium spp., Enterococcus spp., Propionibacterium spp. and Oenococcus spp.

The use of the terms "a" and "an" and "the" and similar referents in the context of describing the invention (especially in the context of the following claims) are to be construed to cover both the singular and the plural, unless otherwise indicated herein or clearly contradicted by context. Thus, "a" and "an" and "the" may mean at least one, or one or more.

The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Any combination of the above-described elements, aspects and embodiments in all possible variations thereof is encompassed by the invention unless otherwise indicated herein or otherwise clearly contradicted by context.

EXAMPLES

Materials and Methods

Fermentation Set-Up

Figure 1:
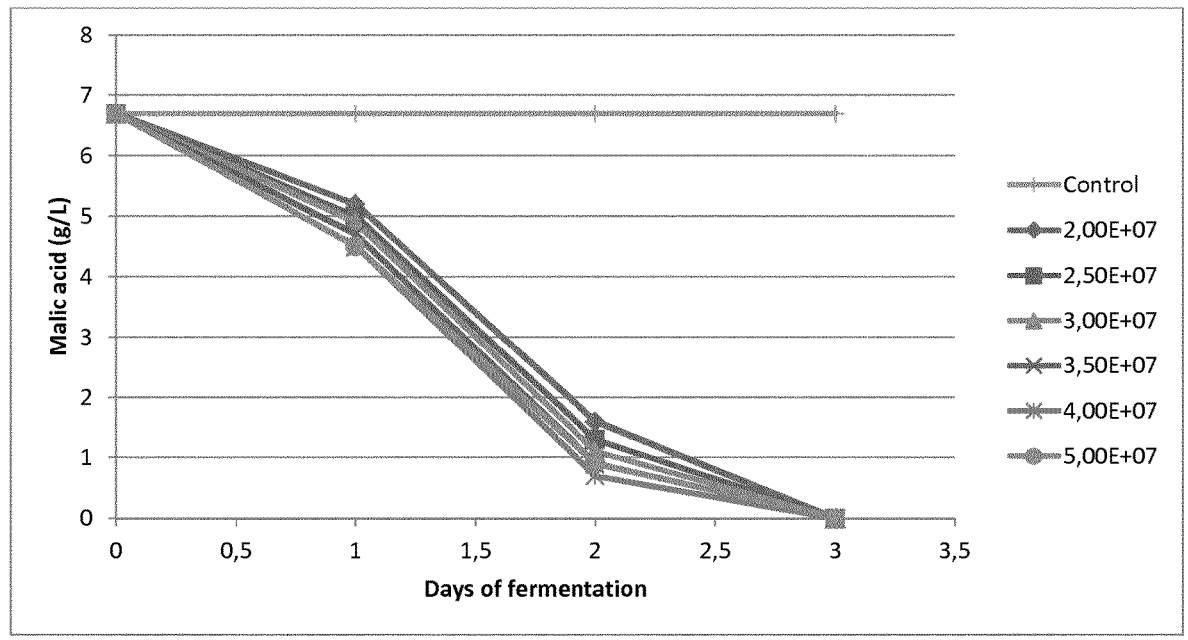
FIG. 1 shows the malolactic activity of different Lactobacillus plantarum strain CHCC12399 inoculation dosages with a Saccharomyces cerevisiae wine yeast in Riesling juice. As control, a fermentation with only Saccharomyces cerevisiae wine yeast is shown.

Lab-scale fermentation trials were carried out in 200 ml of grape juice. Four different grape juices were used: Italian white grape juice, Italian red grape juice, Riesling juice and Hungarian white grape juice. All fermentations were performed at 20° C. until completion (sugar levels<10 g/L). *Lactobacillus plantarum* strain CHCC12399 isolated from South African grape juice, another *Lactobacillus plantarum* strain or a *Lactobacillus paracasei* strain was inoculated at different inoculation levels, ranging from $5 \times 10^6$ to $5 \times 10^7$ CFU/ml. *Saccharomyces cerevisiae* wine yeast was inoculated at $1 \times 10^6$ CFU/ml.

Headspace GC-FID Analysis

Headspace gas chromatography coupled with flame ionisation detection (GC-FID) was used for the measurement of esters and higher alcohols in the fermentation products. Fermentation samples were centrifuged, after which 2 ml was collected in vials. Samples were then analyzed with a calibrated Perkin Elmer GC System with a headspace sampler. The GC was equipped with a DB-WAXETR column (length, 30 m; internal diameter, 0.25 mm; layer thickness, 0.5 μm; Agilent Technologies, Germany). The split-splitless injector was used and held at 180° C. Samples were heated for 30 min at 70° C. in the headspace autosampler before injection (needle temperature: 110° C.). Helium was used as the carrier gas. After starting at 60° C., the oven temperature was raised after 2 min from 60° C. to 230° C. at 45° C./min and was finally held at 230° C. for 5 min. During the GC-program a constant flow rate (10 mL/min) of the carrier gas (He) was maintained. The FID temperature was kept constant at 220° C. respectively. The results were analyzed with Turbochrom software.

Sensory Analysis

Sensory analysis was performed with a professional tasting panel.

Final Wine Parameter Analysis

Ethanol, total sugar (glucose+fructose), total acid (TA), volatile acid (VA), pH and malic acid analysis was performed with Oenofoss™ equipment according to the manufacturer's protocol. Lactic acid, glucose, fructose and acetic acid concentrations were measured with HPLC by methods known to the skilled person and as described by e.g. Castellari et al. (2000. An improved HPLC method for the analysis of organic acids, carbohydrates, and alcohols in grape must and wines. Journal of Liquid Chromatography & Related Technologies 23 (13); p. 2047-2056).

Results

Example 1: Reverse Inoculation of Grape Juice with *Lactobacillus plantarum* Strain CHCC12399 and a Wine *Saccharomyces cerevisiae* Yeast Strain The first experiment is performed with a *Lactobacillus plantarum* strain CHCC12399 isolated from grape juice, which was below pH 3.5. Lab trials with the *Lactobacillus plantarum* strain have been performed in both Italian red and white grape juice. The *Lactobacillus plantarum* strain used here comes as a product in a frozen format (frozen pellets).

*Lactobacillus plantarum* was inoculated at several dosages (ranging from $5 \times 10^6$ to $5 \times 10^7$ CFU/ml) in a reverse inoculation with a wine *Saccharomyces cerevisiae*, inoculated after 72 h at level of $1 \times 10^6$ CFU/ml. The fermentation volume was 200 ml. The initial parameters of the grape juice are described in Table 2.

TABLE 2

Initial parameters of red and white grape juice

| Samples | Glu/Fru* (g/L) | pH | Malic acid (g/L) | TA** (g/L) | Ethanol % (v/v) | VA*** (g/l) |
|---|---|---|---|---|---|---|
| Italian white grape juice | 162.5 | 3.52 | 3.0 | 4.1 | 0 | 0.20 |
| Italian red grape juice | 162.5 | 3.52 | 3.0 | 4.1 | 0 | 0.20 |

*Glu/Fru = sum of glucose and fructose
**TA = total acidity
***VA = volatile acidity In total, 4 conditions have been tested for each grape juice:
  Control: only adding *Saccharomyces cerevisiae*
  $5 \times 10^6$ CFU/ml *Lactobacillus plantarum* CHCC12399+ *Saccharomyces cerevisiae* after 72 h
  $1 \times 10^7$ CFU/ml *Lactobacillus plantarum* CHCC12399+ *Saccharomyces cerevisiae* after 72 h
  $5 \times 10^7$ CFU/ml *Lactobacillus plantarum* CHCC12399+ *Saccharomyces cerevisiae* after 72 h When the fermentations were finished (when sugar was depleted), alcohol level and 10 other relevant wine parameters were measured (Table 3 and 4).

TABLE 3

Final wine parameters in the red wine

| Red wine | Malic acid (g/L) | Lactic acid (g/L) | Glucose (g/L) | Fructose (g/L) | Ethanol (vol %) | Acetic acid (g/L) |
|---|---|---|---|---|---|---|
| Control | 2.28 | 0.12 | 0.08 | 0.42 | 9.50 | <LOD |
| 5.00E+06 CFU/ml | 1.57 | 0.62 | 0.07 | 0.50 | 9.35 | <LOD |
| 1.00E+07 CFU/ml | 0.90 | 1.18 | 0.08 | 0.52 | 9.25 | <LOD |
| 5.00E+07 CFU/ml | <LOD | 4.23 | 0.07 | 0.28 | 8.40 | 0.11 |

TABLE 4

Final wine parameters in the white wine

| White wine | Malic acid (g/L) | Lactic acid (g/L) | Glucose (g/L) | Fructose (g/L) | Ethanol (vol %) | Acetic acid (g/L) |
|---|---|---|---|---|---|---|
| Control | 2.16 | 0.12 | 0.09 | 2.23 | 9.00 | <LOD |
| 5.00E+06 CFU/ml | 1.32 | 0.88 | 0.07 | 1.50 | 9.15 | <LOD |
| 1.00E+07 CFU/ml | 0.29 | 2.09 | 0.08 | 1.68 | 8.85 | <LOD |
| 5.00E+07 CFU/ml | 0.13 | 3.86 | 0.07 | 1.36 | 8.00 | 0.04 |

From Table 3 and 4, it is clear that the wine inoculated with $5 \times 10^7$ CFU per ml *Lactobacillus plantarum* had ≥1% less alcohol (v/v), compared to the control wine and this was the case for both the red and white wine. Interestingly, the dosage of *Lactobacillus plantarum* seems of high importance to reach the lower alcohol percent, as inoculation of $1 \times 10^7$ CFU/ml has no significant effect on the alcohol level. From Table 4, it is can also be seen that addition of *Lactobacillus plantarum* has no negative effect on the acetic acid production, as the concentrations are similar between the control and all dosages of *Lactobacillus plantarum*. However, it is believed that lower dosages of *Lactobacillus plantarum* will also reduce alcohol, depending on the time of inoculation of yeast afterwards; the longer *Lactobacillus plantarum* are allowed to ferment alone, the more sugar will be converted to lactic acid or other metabolites. It is also clear that no more acetic acid is produced when adding the *Lactobacillus plantarum*.

As more lactic acid is produced than is theoretically possible from malic acid, part of the glucose and fructose is converted to lactic acid, leaving less sugar to be converted to ethanol (Table 5). As can be seen in Table 5, more than 16 g/L sugar (glucose and fructose) has been consumed by *Lactobacillus plantarum* in the first 24 hours. This was very surprising, as it was expected that only malic acid would have been consumed under these conditions. 1% of ethanol (v/v) corresponds to 16 g/L of sugar consumed by *Lactobacillus plantarum*. If all sugar would be converted to lactic acid, at least 16 g/L of lactic acid should be formed. As this is not the case, either other metabolic products are formed from glucose or the lactic acid reacts with other metabolic products present during fermentation to form yet another set of metabolic products.

TABLE 5

Sugar measurements 24 h after inoculation of *Lactobacillus plantarum*, before adding the wine yeast

| Inoculation rate of *L. plantarum* | Glu/Fru* (g/L) after 24 h | ΔGlu/Fru* (g/L) 24 h |
|---|---|---|
| 5.00E+06 CFU/ml | 179.7 | 2.6 |
| 1.00E+07 CFU/ml | 170.7 | 11.6 |
| 5.00E+07 CFU/ml | 165.0 | 17.4 |
| Control (no *L. plantarum* added) | 182.3 | 0.0 |

*Glu/Fru = sum of glucose and fructose

To confirm that $5 \times 10^7$ CFU/ml of *Lactobacillus plantarum* is needed to reduce the final alcohol percentage in wine with 1% (v/v), another set of experiments was performed. In this experiment, inoculation levels between $1 \times 10^7$ CFU/ml and $5 \times 10^7$ CFU/ml *Lactobacillus plantarum* were tested for their effect on ethanol production. As adding the wine yeast after 72 h is not commercially viable, the wine yeast was added after 24 h. In this case, Riesling juice was used for the fermentation experiments. The initial parameters of the Riesling juice are given in Table 6.

TABLE 6

Initial parameters of Riesling grape juice

| Sample | Glu/Fru* (g/L) | pH | Malic acid (g/L) | TA** (g/L) | Ethanol % (v/v) | VA*** (g/L) |
|---|---|---|---|---|---|---|
| Riesling | 180.7 | 3.50 | 6.7 | 7.6 | 0 | 0.39 |

*Glu/Fru = sum of glucose and fructose
**TA = total acidity
***VA = volatile acidity

Figure 2:
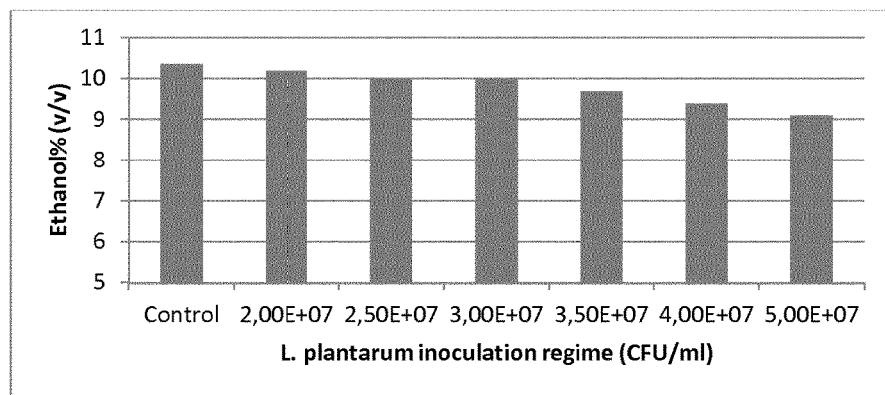
FIG. 2 depicts final alcohol levels in Riesling wine produced with different Lactobacillus plantarum strain CHCC12399 inoculation regimes. A *Saccharomyces cerevisiae* wine yeast has been added after 24 hours of *Lactobacillus plantarum* inoculation. As control, a fermentation with only the *Saccharomyces cerevisiae* wine yeast is shown.

*Lactobacillus plantarum* was added in 6 different inoculation dosages: $2 \times 10^7$ CFU/ml, $2.5 \times 10^7$ CFU/m, $3 \times 10^7$ CFU/ml, $3.5 \times 10^7$ CFU/ml, $4 \times 10^7$ CFU/ml and $5 \times 10^7$ CFU/ml in the Riesling grape juice. After 24 h, a wine *Saccharomyces cerevisiae* strain ($1 \times 10^6$ CFU/ml) was added to the juice to finish the fermentation. The fermentation volume was 200 ml and the fermentation temperature was 20° C. The final wine parameters are shown in Table 6. The malolactic fermentation (MLF) performance and final ethanol levels are depicted in FIGS. 1 and 2.

TABLE 7

Final wine parameters in the Riesling wine

| Samples | Glu/fru* (g/L) | TA** (g/L) | pH | Ethanol % (v/v) | Malic acid (g/L) | VA*** (g/L) |
|---|---|---|---|---|---|---|
| Control | 2.6 | 4.1 | 3.54 | 10.2 | 5.5 | 0.39 |
| 2E7 | 2.6 | 4.2 | 3.55 | 10.2 | 0 | 0.30 |
| 2.5E7 | 2.7 | 4.2 | 3.54 | 10.0 | 0 | 0.30 |
| 3E7 | 2.5 | 4.3 | 3.54 | 10.0 | 0 | 0.30 |
| 3.5E7 | 2.4 | 4.4 | 3.53 | 9.7 | 0 | 0.36 |
| 4E7 | 3.9 | 4.2 | 3.51 | 9.4 | 0 | 0.29 |
| 5E7 | 4.0 | 4.3 | 3.51 | 9.1 | 0 | 0.30 |

*Glu/Fru = sum of glucose and fructose
**TA = total acidity
***VA = volatile acidity The results in Table 7 and FIG. 2 clearly show that $5 \times 10^7$ CFU/ml *Lactobacillus plantarum* is needed to decrease the ethanol percent with 1% (v/v). However, from an inoculation level of $3.5 \times 10^7$ CFU/ml, alcohol level is decreasing in the final wine. On top of that, FIG. 1 shows that MLF is performed during the first three days of fermentation by inoculating *Lactobacillus plantarum* in all dosages.

Example 2: Co-Inoculation of Grape Juice with *Lactobacillus plantarum* Strain CHCC12399 and a Wine *Saccharomyces cerevisiae* Yeast Strain As it is easier to add both *Lactobacillus plantarum* and the yeast together in a so called co-inoculation, it was tested if the ethanol percentage could be reduced in final wine by co-inoculating the *Lactobacillus plantarum* with a *Saccharomyces* wine yeast. In this way, winemakers can add both the *Lactobacillus plantarum* and the wine yeast at the start of a wine fermentation, which makes the new technique easier to use in a commercial way.

For this experiment, the same Riesling juice was used as described in Table 5. *Lactobacillus plantarum* was added at an inoculation dosage of $5 \times 10^7$ CFU/ml, together with the *Saccharomyces cerevisiae* wine yeast ($1 \times 10^6$ CFU/ml). The fermentation was performed at 20° C. Malolactic fermentation (MLF) activity and alcohol production are shown in FIGS. 3 and 4.

Figure 3:
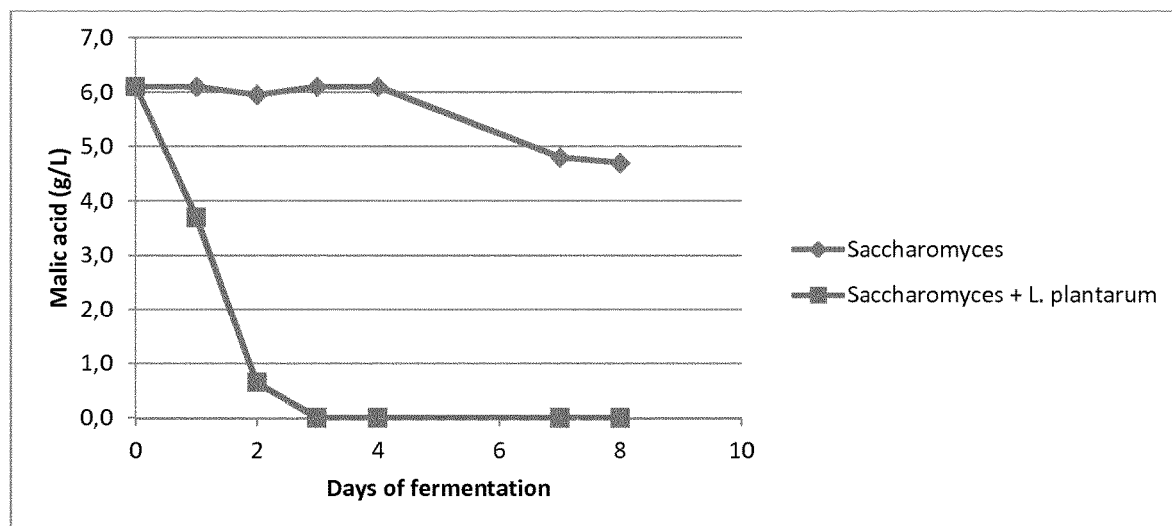
FIG. 3 shows malolactic activity of the *Lactobacillus plantarum* strain CHCC12399 co-inoculated with a *Saccharomyces cerevisiae* wine yeast in Riesling juice. As control, a fermentation with only the *Saccharomyces cerevisiae* wine yeast is shown.
Figure 4:
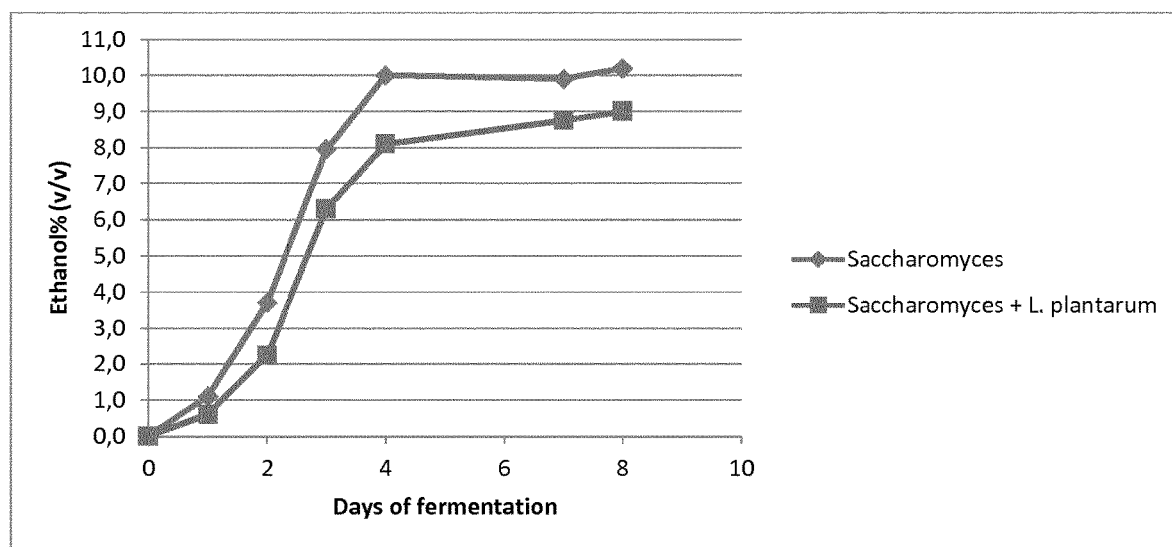
FIG. 4 depicts alcohol production during the fermentation of Riesling juice with the *Lactobacillus plantarum* strain CHCC12399 co-inoculated with a *Saccharomyces cerevisiae* wine yeast. As control, a fermentation with only the *Saccharomyces cerevisiae* wine yeast is shown.

FIGS. 3 and 4 clearly show that co-inoculation of *Lactobacillus plantarum* with a *Saccharomyces cerevisiae* wine yeast results in a final alcohol reduction of 1% (v/v). Also malic acid can be completely degraded when using co-inoculation. This means that co-inoculation of *Lactobacillus plantarum* together with *Saccharomyces cerevisiae* in the correct dosage results in a final alcohol reduction of 1% (v/v) with a completed MLF during the alcoholic fermentation.

Example 3: Reverse Inoculation of Grape Juice with *Lactobacillus plantarum* Strain CHCC12399, *Lactobacillus plantarum* Strain LPL-1 or *Lactobacillus paracasei* Strain LPA-1, Respectively, and a Wine *Saccharomyces cerevisiae* Yeast Strain To investigate if this property of lowering the alcohol content is strain- and/or species-specific, another strain of *Lactobacillus plantarum*, LPL-1, and a *Lactobacillus paracasei* strain, LPA-1, were tested for reducing alcohol (see Table 8). The same protocol was used as before, where the *Saccharomyces cerevisiae* wine yeast was added after 24 h. The *Lactobacillus* strains were inoculated in at a rate of $5 \times 10^7$ CFU/ml and the yeast was added at a rate of $1 \times 10^6$ CFU/ml.

TABLE 8

Final wine parameters in Riesling wine fermented with 3 different *Lactobacillus* strains and a control

| Average | Glu/Fru* (g/L) | TA** (g/L) | Ethanol % (v/v) | Malic acid (g/L) | VA*** (g/L) |
|---|---|---|---|---|---|
| *L. plantarum* CHCC12399 | 6 | 5.75 | 9.1 | 0 | 0.38 |
| *L. plantarum* LPL-1 | 3.65 | 4.8 | 9.5 | 0 | 0.285 |
| *L. paracasei* LPA-1 | 4.35 | 5.6 | 8.65 | 3.9 | 0.31 |
| Only *Saccharomyces* | 7 | 6.35 | 10.05 | 4.5 | 0.31 |

*Glu/Fru = sum of glucose and fructose
**TA = total acidity
***VA = volatile acidity It is very clear from Table 8 that all the tested *Lactobacillus* sp. can reduce alcohol with at least 0.5%. However, it seems that only *Lactobacillus plantarum* has the combined property of reducing alcohol and degrading the malic acid completely.

Example 4: Reverse Inoculation with *Lactobacillus plantarum* Strain CHCC12399 and a Wine *Saccharomyces cerevisiae* Yeast Strain-Field Trials In these experiments, it was tested if this also works in the field. Two trials were set-up in wineries, where the wine *Lactobacillus plantarum* CHCC12399 strain was tested in two different grape varieties: a white grape variety, Chardonnay and a red grape variety, Merlot. In the field trials, it was also tested how the alcohol reduction with *Lactobacillus* sp. affect the flavor profile of the final wine, as this is the main negative issue with using either non-*Saccharomyces* yeast or aeration for reducing alcohol.

In all cases, *Lactobacillus plantarum* was added on the grapes or in the grape juice at the start of fermentation at a dosage of $5 \times 10^6$ CFU/ml and yeast was added after 24 hours. The Chardonnay trial was done in 450 hL tanks and the Merlot trial was performed in 200 hL tanks. In all cases, the initial sugar content was approximately the same and there was a control fermentation carried out with only adding *Saccharomyces* wine yeast. The results are shown in Table 9.

TABLE 9

Final wine parameters in wine trials fermented with and without the wine *Lactobacillus plantarum* strain. Wine yeast was added after 24 h. The control fermentation is a fermentation with only *Saccharomyces* wine yeast.

| Grape variety | Trial | Initial Glu/Fru* (g/L) | Final Glu/Fru* (g/L) | Ethanol % (v/v) | TA** (g/L) | VA*** (g/L) |
|---|---|---|---|---|---|---|
| Chardonnay | Control | 226 | 0 | 14.14 | 4.58 | 0.37 |
| Chardonnay | *L. plantarum* | 229 | 0 | 13.03 | 3.47 | 0.30 |

TABLE 9-continued

Final wine parameters in wine trials fermented with and without the wine *Lactobacillus plantarum* strain. Wine yeast was added after 24 h. The control fermentation is a fermentation with only *Saccharomyces* wine yeast.

| Grape variety | Trial | Initial Glu/Fru* (g/L) | Final Glu/Fru* (g/L) | Ethanol % (v/v) | TA** (g/L) | VA*** (g/L) |
|---|---|---|---|---|---|---|
| Merlot | Control | 250 | 26 | 13.25 | 4.16 | 0.27 |
| Merlot | L. plantarum | 244 | 16 | 12.35 | 4.21 | 0.31 |

*Glu/Fru = sum of glucose and fructose
**TA = total acidity
***VA = volatile acidity The results in Table 9 show that in all field trials, the wine *Lactobacillus plantarum* was able to reduce the final alcohol percent with at least 0.8% (v/v) and this with a very low inoculation rate ($5 \times 10^6$ CFU/ml). This means the proposed technique of using a *Lactobacillus* strain to reduce alcohol with at least 0.5% also works in big scale.

Figure 5:
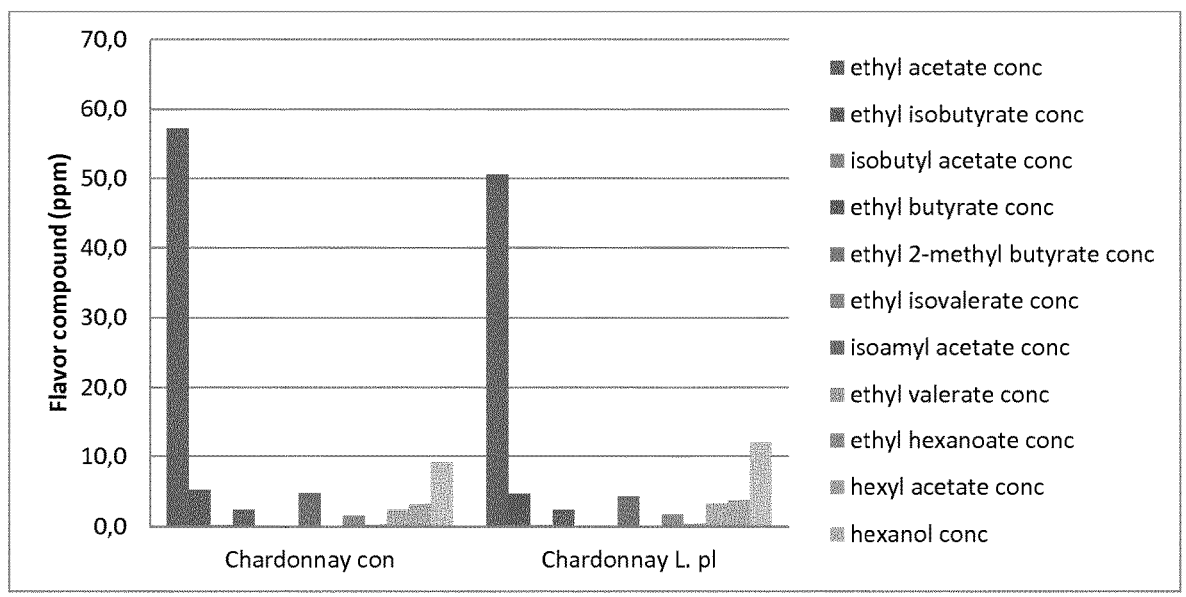
FIG. 5 shows flavor analysis of final Chardonnay wines. Final levels of 11 flavor compounds are shown for both the control Chardonnay wine (only *Saccharomyces* wine yeast; Chardonnay con) and Chardonnay with addition of the *Lactobacillus plantarum* strain CHCC12399 (Chardonnay L. pl).
Figure 6:
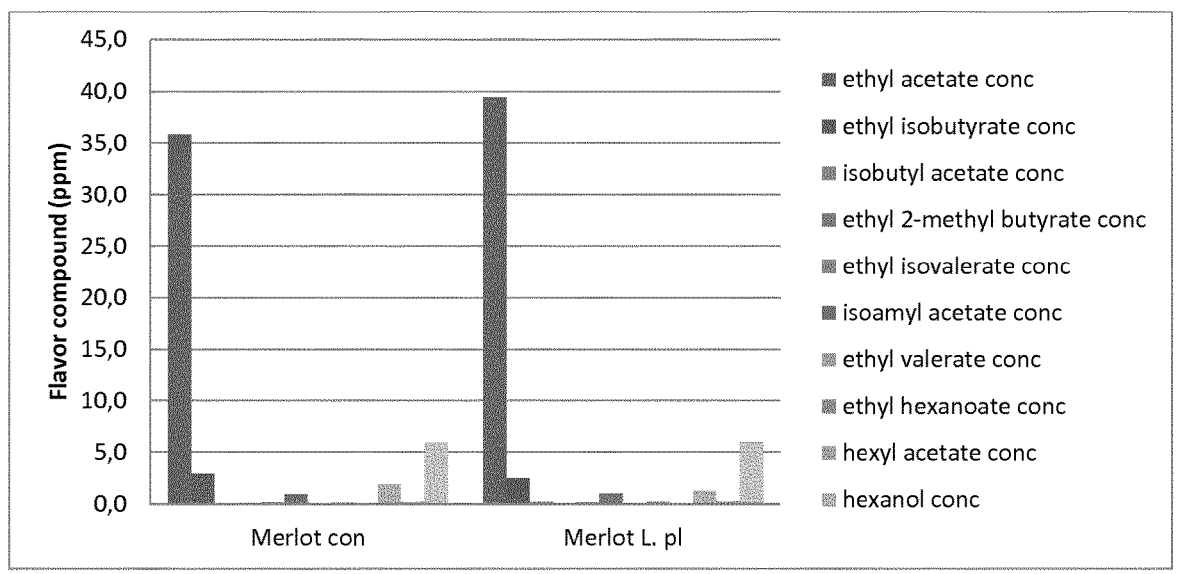
FIG. 6 depicts flavor analysis of final Merlot wines. Final levels of 11 flavor compounds are shown for both the control Merlot wine (only *Saccharomyces* wine yeast; Merlot con) and Merlot with addition of the *Lactobacillus plantarum* strain CHCC12399 (Merlot L. pl).
Figure 7:
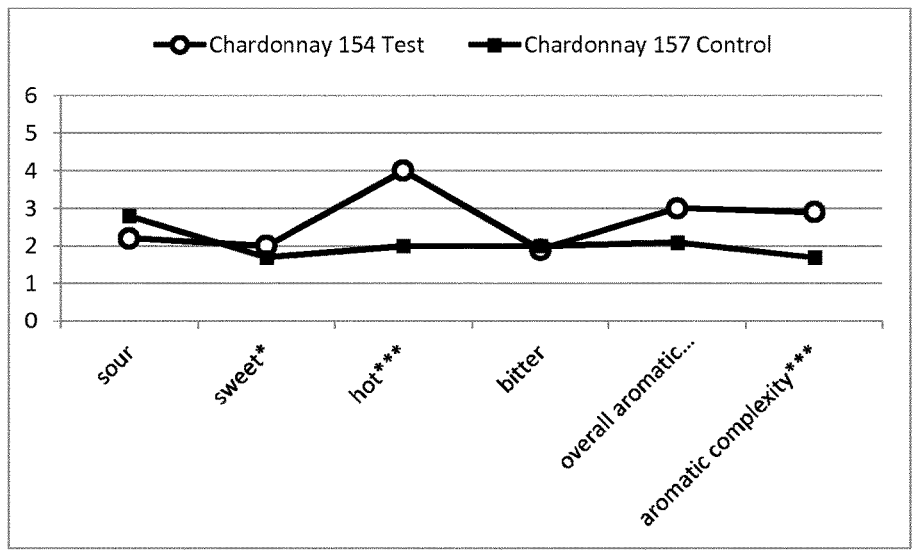
FIG. 7 shows a sensory analysis of final Chardonnay wines. Chardonnay 154 Test is the Chardonnay wine with addition of the *Lactobacillus plantarum* strain CHCC12399 and Chardonnay 157 Control is the control wine (only *Saccharomyces* wine yeast).
Figure 8:
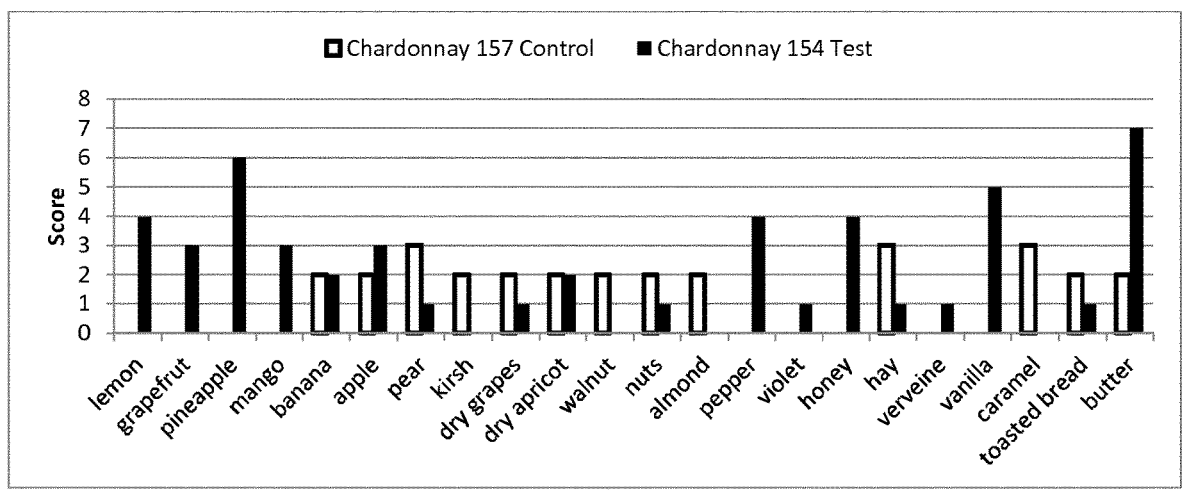
FIG. 8 depicts a sensory descriptive analysis of final Chardonnay wines. Chardonnay 154 Test is the Chardonnay wine with addition of the *Lactobacillus plantarum* strain CHCC12399 and Chardonnay 157 Control is the control wine (only *Saccharomyces* wine yeast).

The wines from Table 9 were analyzed for flavor profile. Furthermore, the Chardonnay wines were analyzed by a professional sensory panel to investigate if the final wines are acceptable with regard to flavor profile compared to the control wines. The sensory panel consisted of 10 people who scored the wines 1 to 5 for each characteristic. The flavor analysis results, performed with headspace-GC-FID, are shown in FIGS. 5 and 6. Sensory analysis results are shown in FIGS. 7 and 8.

As can be seen in both FIGS. 5 and 6, the flavor profile of the Chardonnay control compared with the Chardonnay inoculated with *Lactobacillus plantarum* look very similar. Especially ethyl acetate, which is a main trouble component when non-*Saccharomyces* strains are added, is very similar in both wines and even a bit less in the Chardonnay with addition of *Lactobacillus plantarum*. The same is true for the Merlot wines, also here, the flavor profiles look very similar.

It is very clear from the sensory analysis that the Chardonnay wine with addition of *Lactobacillus plantarum* has certainly no defects compared to the control wine. The test wine is hotter, as shown in FIG. 7, but the overall aromatic intensity and complexity are more preferred in the test wines, compared to the control wine. This is confirmed in the descriptive analysis, where the Chardonnay with the addition of *Lactobacillus plantarum* has a more fruity character (grapefruit, pineapple, mango), compared to the control wine.

Example 5: Reverse Inoculation with Different Time Periods Between Inoculation with *Lactobacillus plantarum* Strain CHCC12399 and Inoculation with Merit Wine Yeast in Hungarian White Grape Juice To investigate the potential of *Lactobacillus plantarum* strain CHCC12399 to reduce alcohol by reducing glucose and/or fructose into lactic acid at the beginning of wine fermentation, experiments were performed in Hungarian white grape juice with the following characteristics (Table 10).

TABLE 10

| Hungarian white grape juice parameters: | | | | | |
|---|---|---|---|---|---|
| Parameters | Glu/Fru (g/l) | pH | Malic acid (g/l) | Total acid (g/l) | Ethanol % (v/v) | VA (g/l) |
| Grape juice | 166.2 | 3.29 | 1.5 | 3.1 | 0 | 0.16 |

The fermentation set-up is described in Table 11. Here it is shown that 6 different set-ups were used: addition of *Lactobacillus plantarum* strain CHCC12399 (NoVA) at the start of fermentation with addition of yeast at different time points afterwards. As control fermentations only yeast were inoculated (exp 11 and 12). The yeast used is Merit inoculated at a concentration of $1 \times 10^6$ CFU/ml. Fermentations were carried out at 20° C.

TABLE 11

| Fermentation set-up | | | |
|---|---|---|---|
| Exp number | NoVa added | Time of yeast inoculation | Total volume |
| 1 | 5E7 CFU/ml | 0 h | 200 ml |
| 2 | 5E7 CFU/ml | 0 h | 200 ml |
| 3 | 5E7 CFU/ml | 24 h | 200 ml |
| 4 | 5E7 CFU/ml | 24 h | 200 ml |
| 5 | 5E7 CFU/ml | 48 h | 200 ml |
| 6 | 5E7 CFU/ml | 48 h | 200 ml |
| 7 | 5E7 CFU/ml | 72 h | 200 ml |
| 8 | 5E7 CFU/ml | 72 h | 200 ml |
| 9 | 5E7 CFU/ml | — | 200 ml |
| 10 | 5E7 CFU/ml | — | 200 ml |
| 11 | — | 0 h | 200 ml |
| 12 | — | 0 h | 200 ml |

Fermentations were carried out until sugar was depleted. During the fermentations, samples were taken for Oenofoss measurements, as well as HPLC measurements for sugars and acids.

Viability of *Lactobacillus* was analysed by anaerobic plating on grape juice agar (GJ5; 77.5 g/L grape juice concentrate (K V Saft Valø), 22.4 g/L yeast extract (Bio Springer), 0.6 g/L Tween® 80 (Sigma-Aldrich), 0.1 g/L $MnSO_4$, $H_2O$ (Merck), 15 g/L agar (SO-BI-GEL) in tap water) with natamyxin (0.075 g/L; Delvocide from DSM Food Specialities B.V.). The plates were incubated for 3 days at 30° C. and then counted.

Viability of yeast was analysed by plating on standard YGC (yeast extract, glucose, chloramphenicol) agar plates. The plates were incubated for 2 days at 30° C. and then counted.

The results shown do not contain experiment number 9 and 10, as spontaneous fermentation with yeast started in these samples and they are therefore considered to be inaccurate. Spontaneous fermentation also started in exp number 7 and 8, but was over seeded with Merit yeast at 72 hours after addition of *Lactobacillus plantarum* strain CHCC12399 (NoVA). The *Lactobacillus* and yeast cell counts are given in FIGS. 9 and 10, respectively. The sugar and acid measurements are shown in FIGS. 11-15.

Figure 9:
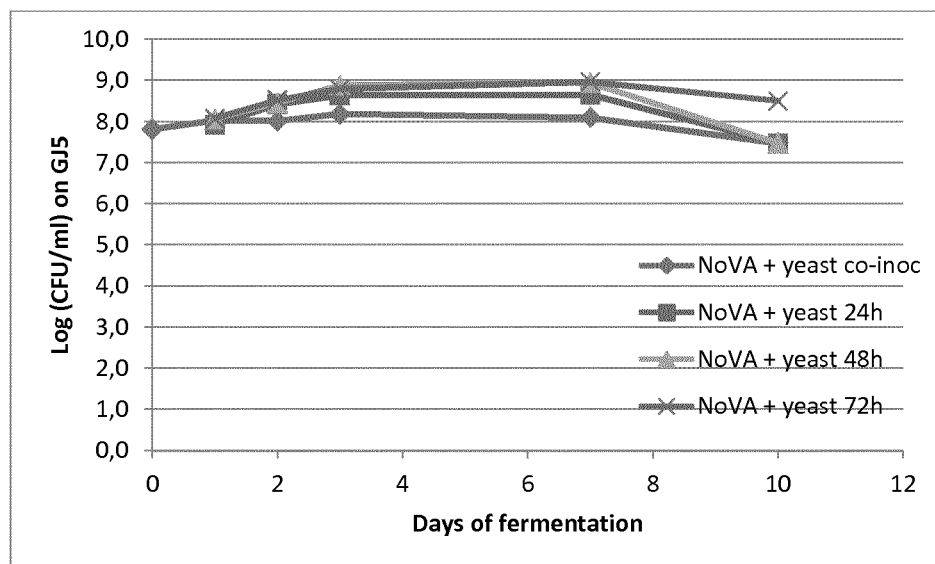
FIG. 9 shows *Lactobacillus* cell counts during fermentation of Hungarian white grape juice with *Lactobacillus plantarum* strain CHCC12399 (NoVA) and Merit wine yeast added at different time points.
Figure 10:
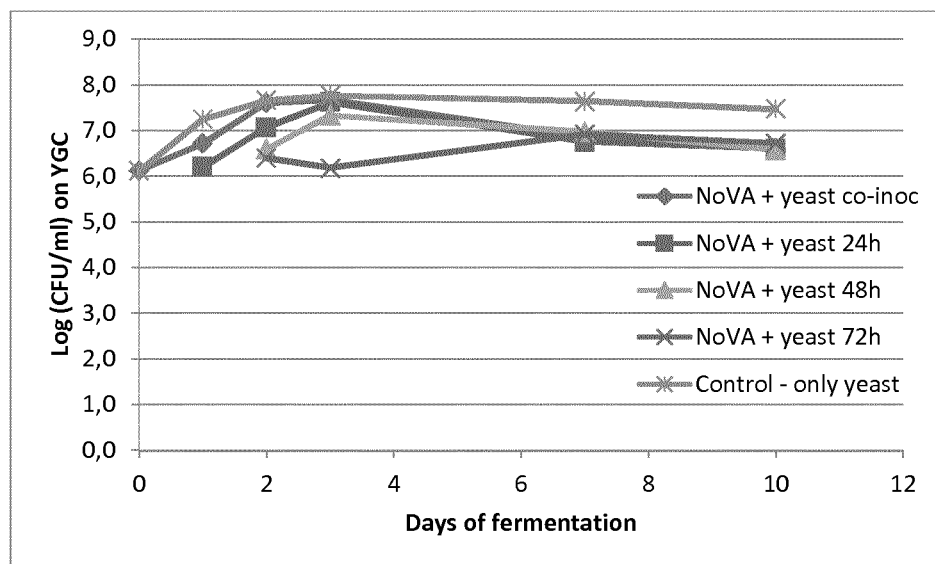
FIG. 10 depicts yeast cell counts during fermentation of Hungarian white grape juice with *Lactobacillus plantarum* strain CHCC12399 (NoVA) and Merit wine yeast added at different time points.
Figure 11:
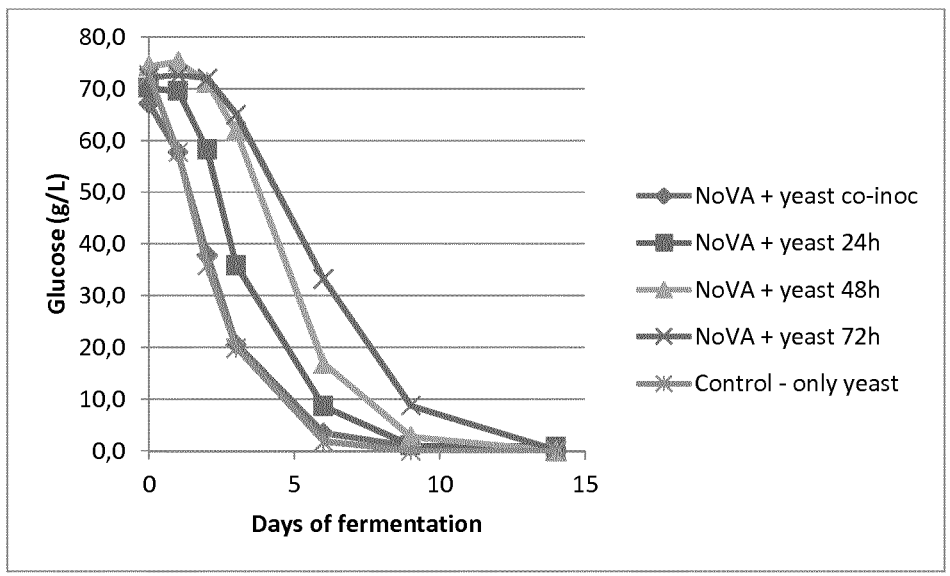
FIG. 11 shows glucose concentrations during fermentation of Hungarian white grape juice with *Lactobacillus plantarum* strain CHCC12399 (NoVA) and Merit wine yeast added at different time points.
Figure 12:
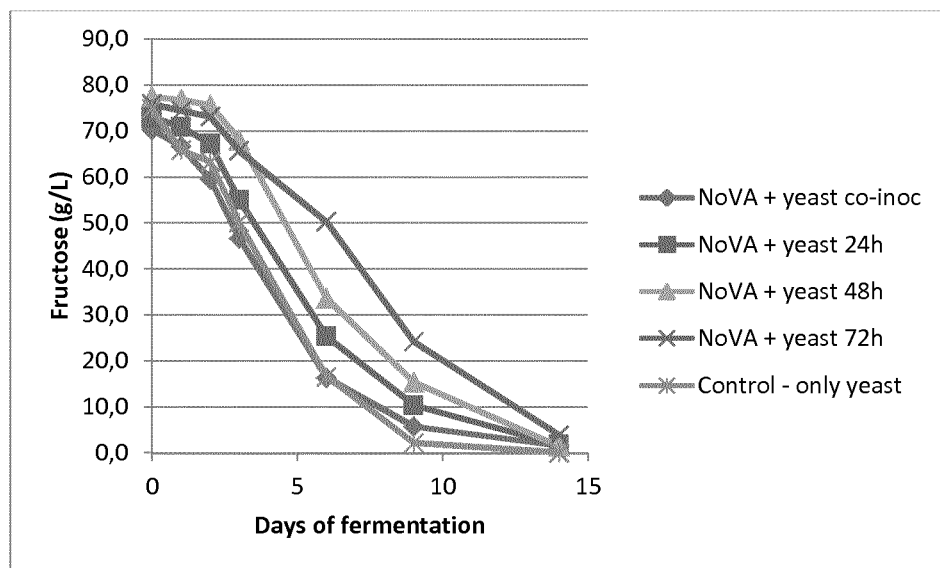
FIG. 12 depicts fructose concentrations during fermentation of Hungarian white grape juice with *Lactobacillus plantarum* strain CHCC12399 (NoVA) and Merit wine yeast added at different time points.
Figure 13:
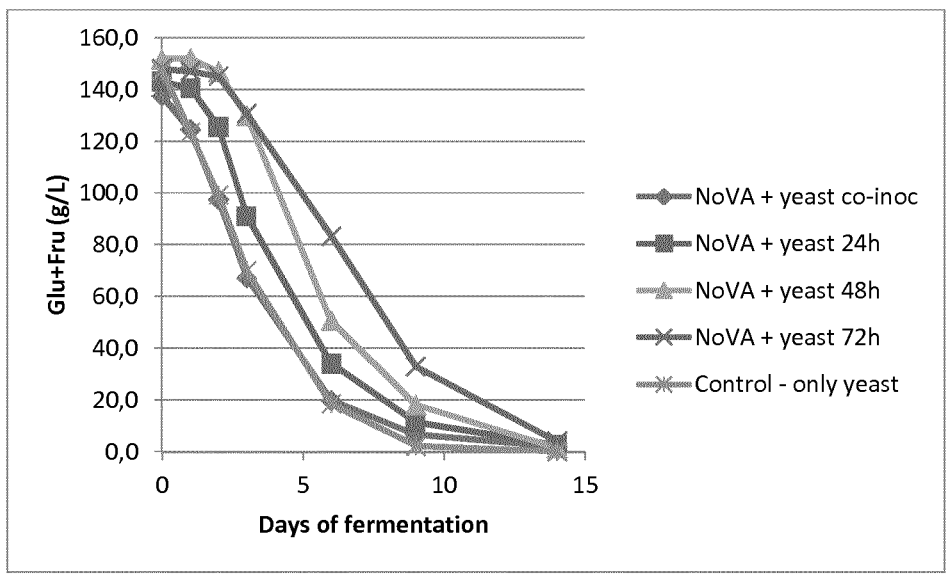
FIG. 13 shows glucose and fructose concentrations during fermentation of Hungarian white grape juice with *Lactobacillus plantarum* strain CHCC12399 (NoVA) and Merit wine yeast added at different time points.
Figure 14:
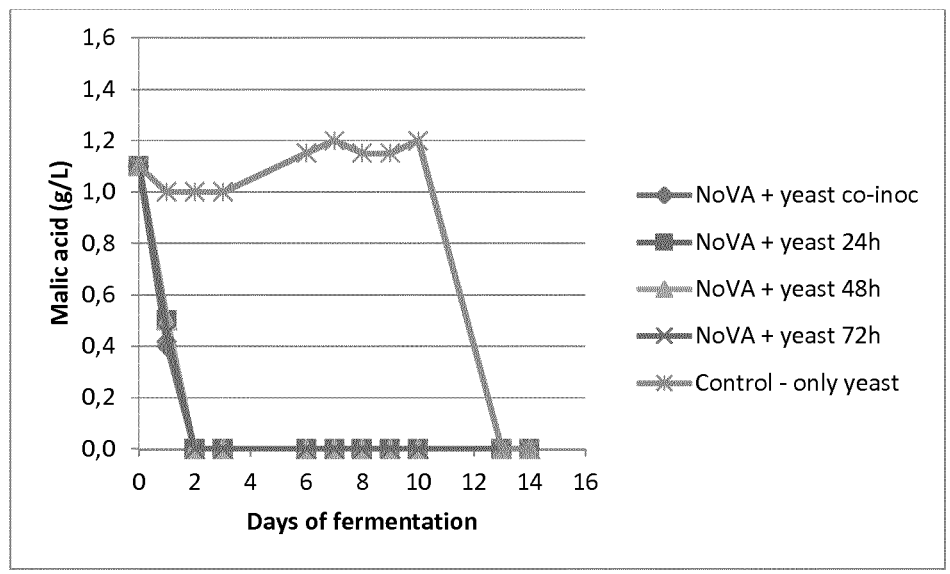
FIG. 14 depicts malic acid concentrations during fermentation of Hungarian white grape juice with *Lactobacillus plantarum* strain CHCC12399 (NoVA) and Merit wine yeast added at different time points.
Figure 15:
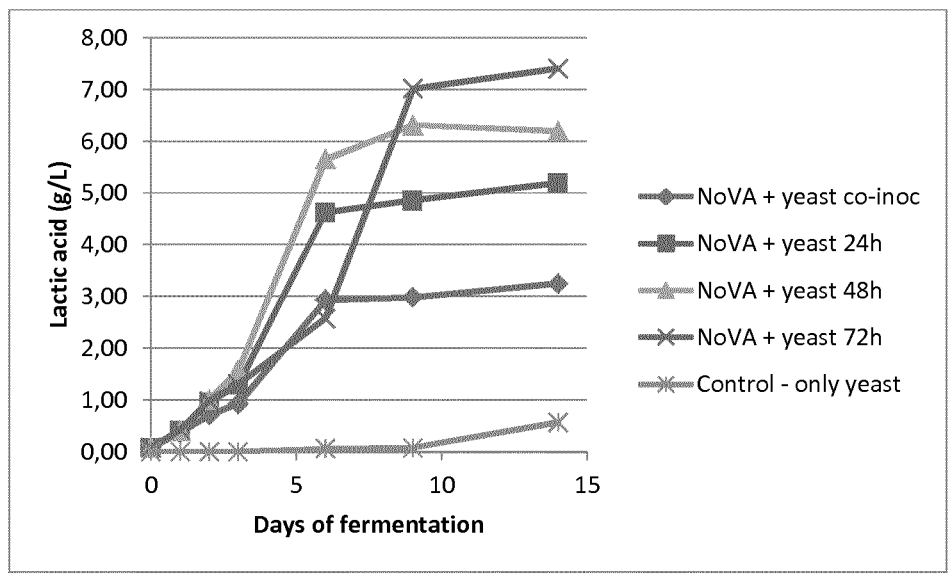
FIG. 15 shows lactic acid concentrations during fermentation of Hungarian white grape juice with *Lactobacillus plantarum* strain CHCC12399 (NoVA) and Merit wine yeast added at different time points.

From the results shown in FIGS. 9 and 10, it is clear that *Lactobacillus plantarum* grew in all experiments, except for the experiment with co-inoculation, where the cell count does not change over time. This could be explained by the fact that yeast counts are already very high at day 1, meaning that *Lactobacillus plantarum* strain CHCC12399 does not have the time to grow. *Lactobacillus plantarum* strain CHCC12399 (NoVA) is still active, though, as malic acid is completely consumed after day 2 (FIG. 14).

Figure 16:
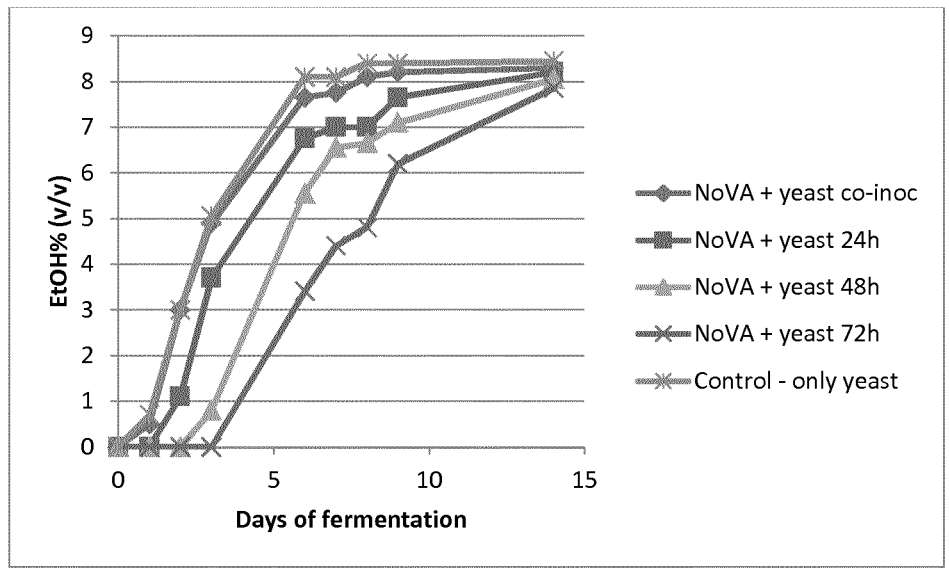
FIG. 16 shows ethanol production during fermentation of Hungarian white grape juice with *Lactobacillus plantarum* strain CHCC12399 (NoVA) and Merit wine yeast added at different time points.

Ethanol concentrations during fermentation are shown in FIG. 16 and final ethanol concentrations are shown in Table 12.

TABLE 12

Final ethanol concentrations of all wines

| NoVA | Yeast | EtOH % (v/v) |
|---|---|---|
| + | 0 h | 8.3 |
| + | 24 h | 8.2 |
| + | 48 h | 8.05 |
| + | 72 h | 7.85 |
| − | 0 h | 8.45 |

It is very clear from the final ethanol concentrations in Table 12 that adding *Lactobacillus plantarum* strain CHCC12399 (NoVA) in a concentration of $5 \times 10^7$ CFU/ml and fermenting 2 or 3 days before the addition of yeast can reduce alcohol levels. Highest alcohol reduction was with yeast inoculation after 3 days in this case, where the final alcohol reduction is 0.6% ethanol (v/v).

From FIGS. 11-14, it is also clear that malic acid needs to be consumed first, before *Lactobacillus plantarum* strain CHCC12399 (NoVA) starts eating sugar. Malic acid is consumed within 2 days for all different scenarios. Even with the co-inoculation of *Lactobacillus plantarum* strain CHCC12399 and yeast, malic acid gets consumed within 2 days after the start of fermentation. Lactic acid is produced from both malic acid and sugar (fructose), resulting in a higher lactic acid production when the yeast is added later. Almost no lactic acid is produced in the control fermentation, where only yeast is added.

It is also clear from the single sugar results in Table 13 that *Lactobacillus plantarum* strain CHCC12399 (NoVA) prefers fructose over glucose.

TABLE 13

Sugar consumption (in g/L) with NoVA, measured before yeast addition

| NoVa | Yeast | Day measured | ΔGlucose | ΔFructose |
|---|---|---|---|---|
| + | 0 h | 0 | 0 | 0 |
| + | 24 h | 1 | 0 | 0 |
| + | 48 h | 2 | 0 | 0.6 |
| + | 72 h | 3 | 0.1 | 2.7 |

*Lactobacillus plantarum* strain CHCC12399 consumes fructose and no glucose before the yeast is added, but must also consume more fructose (and/or glucose) during the start of alcoholic fermentation, in order to decrease the alcohol level with 0.6%.

CONCLUSION

It is clear from this experiment that *Lactobacillus plantarum* strain CHCC12399 can reduce alcohol in final wines by reverse inoculation. The results show that malic acid is assimilated first, before *Lactobacillus plantarum* strain CHCC12399 starts assimilating sugar. It was also surprising to find that *Lactobacillus plantarum* strain CHCC12399 consumes fructose as the main sugar, and does not seem to consume glucose in this case.

DEPOSIT AND EXPERT SOLUTION

The strain of *Lactobacillus plantarum* CHCC12399 was deposited with Deutsche Sammlung von Mikroorganismen and Zellkulturen GmbH, Inhoffenstr. 7B, D-38124 Braunschweig, Germany on 1 Aug. 2013 under the accession number DSM 27565.

The deposit has been made under the conditions of the Budapest Treaty on the International Recognition of the Deposit of Microorganisms for the Purposes of Patent Procedure.

The Applicant requests that a sample of the deposited microorganisms should be made available only to an expert approved by the Applicant.

REFERENCES

Ciani, M., and Ferraro, L. (1996) Enhanced glycerol content in wines made with immobilized *Candida stellata* cells. Applied and Environmental Microbiology, 62:128-132.

Comitini, F., Gobbi, M., Domizio, P., Romani, C., Lencioni, L., Mannazzu, I., and Ciani, M. (2011) Selected non-*Saccharomyces* wine yeasts in controlled multistarter fermentations with *Saccharomyces cerevisiae*. Food Microbiology, 28:873-882.

Contreras, A., Hidalgo, C., Henschke, P. A., Chambers, P. J., Curtin, C., and Varela, C. (2013) Evaluation of non-*Saccharomyces* yeast for the reduction of alcohol content in wine. DOI:10.1128/AEM.03780-13.

Di Maio, S., Genna, V., Gandolfo, V., Amore, G., Ciaccio, M., and Oliva, D. (2012) Presence of *Candida zemplinina* in Sicilian musts and selection of a strain for wine mixed fermentations. South African Journal of Enology and Viticulture, 33:80-87.

Erten, H., and Campbell, I. (2001) The production of low-alcohol wines by aerobic yeasts. Journal of the Institute of Brewing, 107:207-215.

Ferraro, L., Fatichenti, F. and Ciani, M. (2000) Pilot scale vinification process using immobilized *Candida stellata* cells and *Saccharomyces cerevisiae*. Process Biochemistry, 35:1125-1129.

Garcia, V., Vasquez, H., Fonseca, F., Manzanares, P., Viana, F., Martinez, C. et al. (2010) Effects of using mixed wine yeast cultures in the production of Chardonnay wines. Revista Argentina de Microbiologia, 42:226-229.

Grossmann, M., Kruse, R. and Heintz, W. (1991). Producing drinks of low to zero alcohol content—oxygen is added to liquid in controlled manner during fermentation to convert sugars to water and carbon dioxide. DE3939064 (A1).

Kaeppeli, O. (1989). Production of sugar-free or low-sugar fruit juice—by fermentation with yeast to carbon dioxide and water stage, avoiding ethanol production. CH668887 (A5).

Kolb, E., Wiesenberger, A., Stahl, U. and Harwart, K. (1993). Biological processes for the partial reduction of sugar in fruit juices. Proceedings of the International Federation of Fruit Juice Producers Symposium, Budapest, 7-20.

Kutyna, D. R., Varela, C., Henschke, P. A., Chambers, P. A., and Stanley, G. A. (2010) Microbiological approaches to lowering ethanol concentrations in wine. Trends Food Science and Technology, 21:293-302.

Maygar, I. and Toth, T. (2011) Comparative evaluation of some oenological properties in wine strains of *Candida*

*stellata Candida zemplinina, Saccharomyces uvarum* and *Saccharomyces cerevisiae*. Food Microbiology, 28:94-100.

Pickering G. J. (2000). Low and reduced-alcohol wines: a review. Journal of Wine Research, 11:129-144.

Sadoudi, M., Tourdot-Marechal, R., Rousseaux, S., Steyer, D., Gallardo-Chacon, J. J., Ballester, J., Vichi, S., Guerin-Schneider, R., Caixach, J., and Alexandre, H. (2012) Yeast-yeast interactions revealed by aromatic profile analysis of Sauvignon Blanc wine fermented by single or co-culture of non-*Saccharomyces* and *Saccharomyces yeasts*. Food Microbiology, 32:243-253.

Schmidtke, L. M., Blackman, J. W., and Agboola, S. O. (2012) Production technologies for reduced alcoholic wines. Journal of Food Science, 71:25-41.

Smith, P. M. (1995) Biological processes for the reduction of alcohol in wines. M. Appl. Sci., dissertation, Lincoln University, New Zealand.

The invention claimed is:

1. A method for producing a fermented fruit beverage having a reduced alcohol content, comprising:
    (a) inoculating a fruit must with at least one *Lactobacillus plantarum* strain in an amount of at least $5 \times 10^6$ CFU/ml and fermenting the fruit must with the at least one *Lactobacillus plantarum* strain for at least 24 hours; and
    (b) after fermenting the fruit must with the at least one *Lactobacillus plantarum* strain for at least 24 hours, fermenting the fruit must with at least one yeast strain to obtain a fermented fruit beverage,
    wherein at least a portion of sugar in the fruit must is converted by the fermenting with the at least one *Lactobacillus plantarum* strain prior to the fermenting with the at least one yeast strain,
    wherein the fermented fruit beverage is selected from red wine, white wine, sparkling wine and cider, and has an alcohol content after step (b) of at least 4% (v/v), wherein the alcohol content of the fermented fruit beverage after step (b) is at least 0.5% (v/v) less than the alcohol content of a fermented fruit beverage prepared by the same method but without inoculating and fermenting the fruit must with the *Lactobacillus plantarum* strain(s).

2. The method according to claim 1, wherein the at least one *Lactobacillus plantarum* strain is selected from the group consisting of the *Lactobacillus plantarum* strain CHCC12399 that was deposited with the German Collection of Microorganisms and Cell Cultures (DSMZ) under accession No. DSM 27565, and functionally equivalent mutant strains thereof, wherein the mutant strains are obtained by using the deposited strain as starting material and wherein less than 1% of the nucleotides of the mutant strain are changed as compared to the mother strain, and wherein the mutant strains, when used to inoculate and ferment a fruit must prior to or simultaneously with fermentation of the fruit must with at least one yeast strain, result in a fermented fruit beverage having an alcohol content less than that of a fermented fruit beverage prepared by the same method comprising fermenting with the same yeast strain(s) but without inoculating and fermenting with the mutant strain.

3. The method according to claim 1, wherein the at least one *Lactobacillus plantarum* strain comprises the *Lactobacillus plantarum* strain CHCC12399 that was deposited with the German Collection of Microorganisms and Cell Cultures (DSMZ) under accession No. DSM 27565.

4. The method according to claim 1, wherein the fruit must is fermented with the yeast strain within 72 hours after being inoculated with the at least one *Lactobacillus plantarum* strain.

5. The method according to claim 1, wherein the at least one yeast strain includes a yeast strain of a species selected from *Pichia kluyveri, Saccharomyces cerevisiae, Saccharomyces pastorianus, Saccharomyces bayanus, Torulaspora delbrueckii*, and *Kluveromyces thermotolerans*.

6. The method according to claim 1, wherein one yeast strain is used in step (b).

7. The method according to claim 1, wherein two or more yeast strains are used in step (b).

8. The method of claim 1, wherein at least 5 g/L sugar in the fruit must is converted by the fermenting with the at least one *Lactobacillus plantarum* strain prior to the fermenting with at least one yeast strain.

9. The method of claim 1, wherein the fermented fruit beverage contains less than 10 g/L sugar following the fermenting with the at least one yeast strain.

* * * * *